United States Patent [19]

Sales

[11] 4,258,698
[45] Mar. 31, 1981

[54] SOLAR HEATING APPARATUS

[76] Inventor: Franklin D. Sales, 333 Mamaki St., Honolulu, Hi. 96821

[21] Appl. No.: 74,086

[22] Filed: Sep. 10, 1979

[51] Int. Cl.³ .................................................. F24J 3/02
[52] U.S. Cl. ..................................... 126/440; 126/450; 126/451
[58] Field of Search ............... 126/440, 450, 451, 442, 126/424, 425, 446, 417, 441

[56] References Cited

U.S. PATENT DOCUMENTS

| | | | |
|---|---|---|---|
| 696,326 | 3/1902 | De La Garza | 126/440 |
| 1,081,098 | 12/1913 | De La Garza | 126/440 |
| 1,479,923 | 1/1924 | Moreau | 126/440 |
| 1,951,403 | 3/1934 | Goddard | 126/440 |
| 2,920,710 | 1/1960 | Howard | 126/424 |
| 3,915,148 | 10/1975 | Fletcher | 126/440 |
| 3,970,070 | 7/1976 | Meyer et al. | 126/440 |
| 4,000,733 | 1/1977 | Pauly | 126/440 |
| 4,064,865 | 12/1977 | Depew | 126/440 |
| 4,092,979 | 6/1978 | Kotlarz | 126/440 |
| 4,139,286 | 2/1979 | Hein et al. | 126/440 |

FOREIGN PATENT DOCUMENTS

| | | | |
|---|---|---|---|
| 547475 | 8/1956 | Italy | 126/440 |
| 32139 | 3/1977 | Japan | 126/440 |

*Primary Examiner*—Daniel J. O'Connor
*Attorney, Agent, or Firm*—George W. T. Loo

[57] ABSTRACT

A solar heating apparatus that uses a Fresnel lens to concentrate solar radiation onto the top surface of a heat conductor for the purpose of heating a transient fluid or gas. The apparatus includes a conductor, a frame, and a Fresnel lens. The conductor and Fresnel lens are secured to the frame so that the conductor is within the optimum focal position of the Fresnel lens. A helical conduit around the periphery of the core of the conductor with a larger diameter than the diameter of the inlet and outlet conduits of the conductor provides additional residence time for the fluid or gas. A number of apparatus may be joined together in a series of rows so that the fluid or gas may be heated to an extremely high temperature. The heated fluid or gas may be used to power a turbine for the generation of electrical power or to supply process heat for commericial or industrial use.

6 Claims, 8 Drawing Figures

SOLAR HEATING APPARATUS

BACKGROUND OF THE INVENTION

1. Field of Invention

This invention relates to the collection of solar energy by use of a focusing lens that focuses solar radiation onto a heat conductor for the purpose of heating a transient fluid or gas.

2. Description of the Prior Art

Prior art devices usually consist of complex assemblies of reflectors, conduits, holding vessels with solar heated probes, multiple lens assemblies, and structural support assemblies that render the devices impractical for use other than in experimental or very large installations. My invention is very simple and economical to assemble and use. Yet it will provide heated fluids or gases at a very economical and practical cost for small or large installations with a solar radiation concentration ratio of over 1000 to 1.

3. Disclosure Statement

Bard, U.S. Pat. No. 3,985,118, issued Oct. 12, 1976, discloses a solar furnace wherein multiple Fresnel lenses focus solar radiation upon heat conductors associated with each of the lenses. Control means are provided to allow such lens assembly to follow the apparent travel of the sun.

Trihey, U.S. Pat. No. 3,996,917, issued Dec. 14, 1976, discloses a solar heating apparatus for heating a pumped heat transfer medium as it passes a solar absorbing target located at the focal region of the light focusing means. Tracking means are provided to ensure that the optical axis of the focussing means is pointed directly at the sun.

Diggs, U.S. Pat. No. 4,030,890, issued June 21, 1977, discloses a device which utilizes solar energy to transform water into steam and steam into hydrogen and oxygen through dissociation. The steam in the dissociating means is forced to traverse a spiral path wherein it undergoes a circuit motion to subject it to centrifugal force while contacting a heat transfer surface. Control program moves a solar reflecting mirror as the angle of the sun is changed by rotation of the earth.

Weslow, U.S. Pat. No. 4,137,899, issued Feb. 6, 1979, discloses a multistage solar energy concentrator wherein a plurality of lenses are secured in the top of a housing and near the bottom of the housing is a first fluid conduit located at the foci of the lenses for absorbing primary solar radiation focused thereon.

My invention is not anticipated by the above cited patents, either individually or collectively. My invention would not be obvious to a person having ordinary skill in the solar energy art because if it were, some one would have made it prior to my inventing it. My invention is simple and inexpensive to contruct. Yet it will provide a heated fluid or gas at a very economical and practical cost for small or large installations.

SUMMARY OF THE INVENTION

This invention relates to the collection of solar energy by use of a number of Fresnel lenses that will focus solar radiation onto a corresponding number of heat conductors for the purpose of heating a pressurized fluid or gas.

An object of this invention is to provide a solar heating apparatus which is simple and inexpensive to manufacture and to use.

Another object of this invention is to provide a solar heat conductor which has a helical channel around the periphery of its core to utilize the maximum surface area of the core.

A further object of this invention is to provide a solar heating apparatus wherein a multiple of solar energy heat conductors are connected together in a row or a series of rows so that a pressurized fluid or gas may be heated to extremely high temperatures.

Still another object of this invention is to provide a solar heating apparatus wherein multiple Fresnel lenses focus light rays upon heat conductors associated with each of the lenses.

A still further object of this invention is to provide a solar heating apparatus wherein the heat conductor is positioned within the optimum focal point of a Fresnel lens.

Another object of this invention is to provide a solar heating apparatus which is adapted to be mounted on a two axis tracking device.

Other objects, features and advantages of the present invention will be readily apparent from the following detailed description taken in connection with the accompanying drawings.

DESCRIPTION OF THE PREFERRED EMBODIMENT

Figure 1:
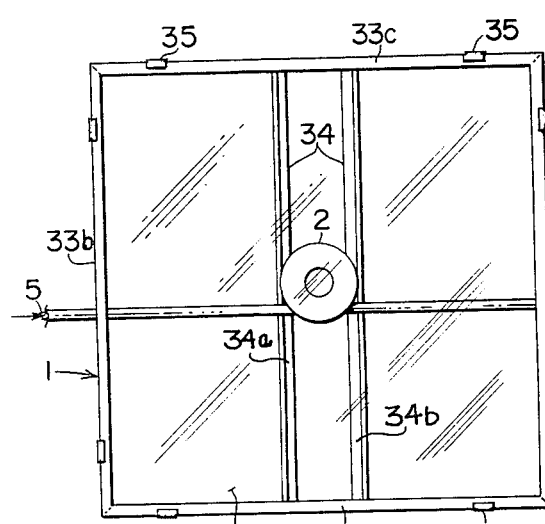
FIG. 1 is a plan view of the invention.
Figure 2:
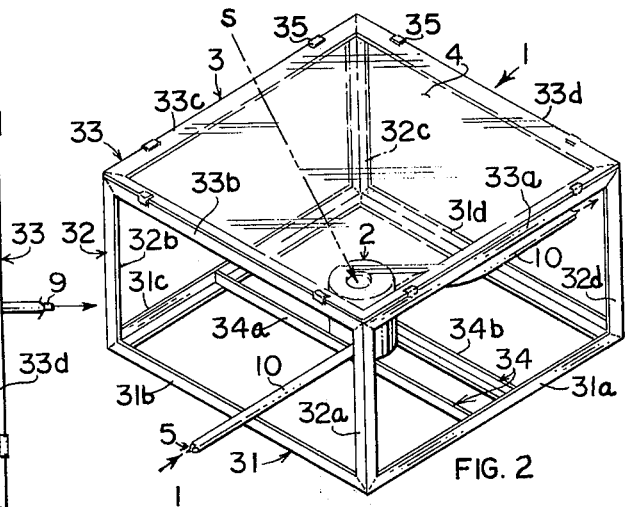
FIG. 2 is a perspective view of the invention with a sun ray being focused on the top of the core.
Figure 3:
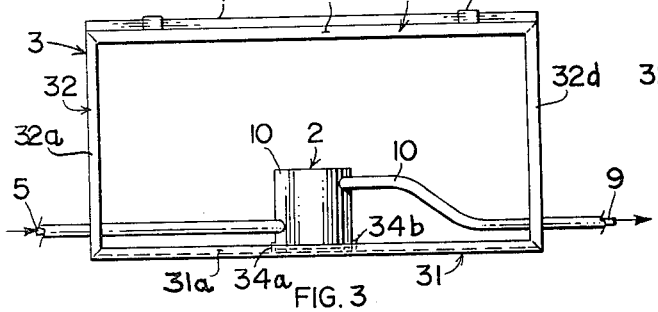
FIG. 3 is a front elevation view of the invention.
Figure 4:
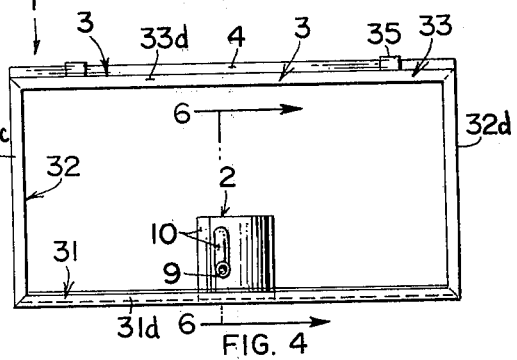
FIG. 4 is a right elevation view of the invention.

Before explaining the present invention in detail it is to be understood that the invention is not limited in its application to the details of construction and arrangement of parts illustrated in the accompanying drawings, since the invention is capable of other embodiments and of being practiced or carried out in various ways. Also, it is to be understood that the phraseology or terminology employed herein is for the purpose of description and not of limitation.

Referring now to the drawings wherein like reference numerals refer to like and corresponding parts throughout the several views, the preferred embodiment of the invention disclosed in FIGS. 1-8 inclusive is a solar heating apparatus 1. Apparatus 1 includes a heat conductor 2, metal frame 3, and Fresnel lens 4. See FIG. 2.

Conductor 2 includes an inlet conduit 5, a housing 6, a core 7, pressure plate 8, and outlet conduit 9. Housing 6 includes a cylindrical opening 11, a central opening 12, a cylindrical opening 13, an inner flange 14, an outer flange 15, and two openings 16. Inlet conduit 5 is connected at 17 to one side of housing 6 and is in communication with cylindrical opening 11. Outlet conduit 9 is connected at 18 to the other side of housing 6 and is in communication with cylindrical opening 13.

Core 7 includes a body 24, a head 25, spiral grooves 26, and top surface 19. Spiral grooves 26 revolve around the periphery of body to form a helical channel for a transient fluid or gas. One end of the spiral grooves 26 communicates with cylindrical opening 11 and the other end communicates with cylindrical opening 13. See FIG. 7.

Pressure plate 8 includes a center opening 20 and two openings 21 near its circumference. Pressure plate 8 is secured to outer flange 15 by means of two bolts 22 which pass through openings 21 and 16. Center opening 20 allows impinging focused solar radiation onto top surface 19. See FIG. 6. Reference letter S in FIGS. 2 and 6 denotes the Sun. The arrow with a broken shaft denotes the ray of the Sun.

Frame 3 includes a bottom portion 31, a side portion 32, a top portion 33, and a connector portion 34. Bottom portion 31 includes four angle irons 31a, 31b, 31c, and 31d which are connected at their ends to form a rectangular structure. Side portion 31 includes four angle irons 32a, 32b, 32c, and 32d which are placed upright at the corners of bottom portion 31 and are secured thereto by welding. Top portion 33 includes four angle irons 33a, 33b, 33c, and 33d which are connected at their ends to form a rectangular structure and secured to side portion 32 by welding. Connector portion 34 includes two spaced angle irons 34a and 34b which are secured at their ends to angle irons 31a and 31c. Angle irons 34a and 34b are spaced so that conductor 2 will fit within the legs of the angle irons. Conductor 2 is secured to angle irons 34a and 34b by welding. See FIGS. 1-3.

Fresnel lens 4 is held onto top portion 33 by metal fasteners 35, which are punched out of top portion 33. Fresnel lens 4 concentrates solar radiation onto the top surface 19 of core 7. Core 7 is positioned within the optimum focal point of the lens when conductor 2 is secured to frame 3. Center opening 20 allows impinging focused solar radiation onto the top surface 19. See FIG. 6.

Inlet conduit 5, housing 6, pressure plate 8, and outlet conduit 9 are made of stainless steel. Core 7 is made of a high heat conductivity material such as that afforded by copper. Spiral grooves 26 revolve around the periphery of body 24 two and one half times. Top surface 19 is coated with a coating of black chrome on nickel to increase absorption of solar radiations. Conductor 2 is coated with a suitable solid insulation 10 such as asbestos or calcium silicate.

Figure 5:
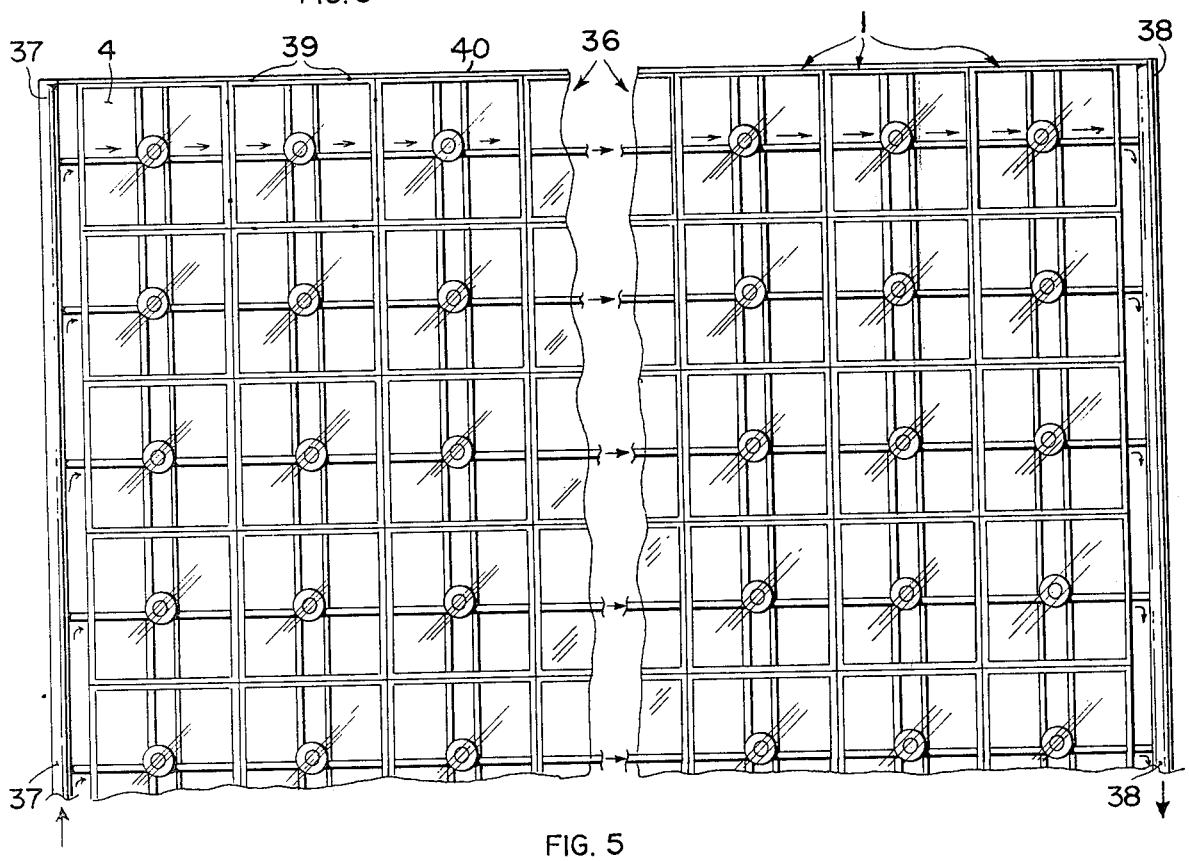
FIG. 5 is a plan view of the invention to illustrate how it is connected to other units to form a modular panel.
Figure 6:
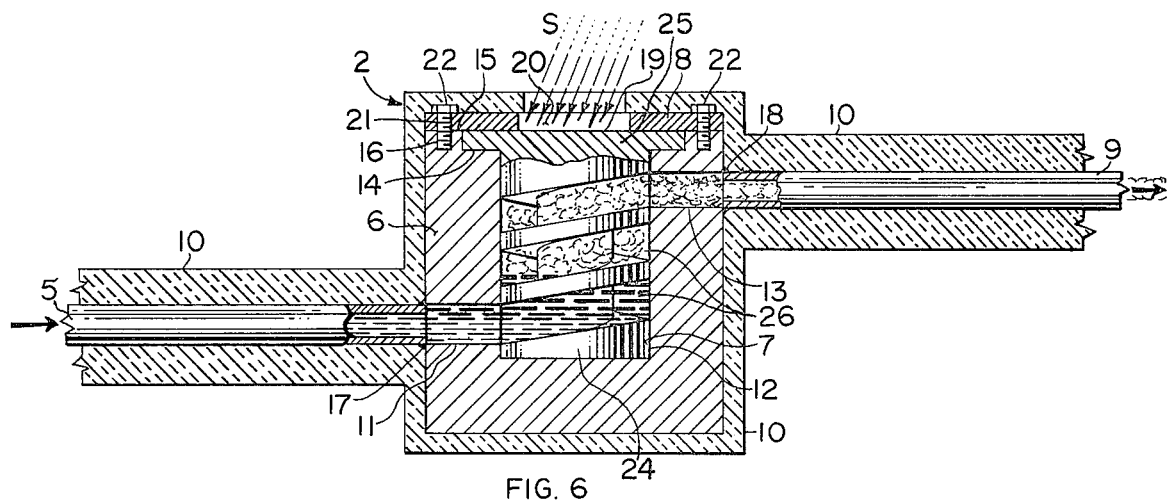
FIG. 6 is an enlarged sectional view of the invention taken on line 6—6 of FIG. 4.
Figure 7:
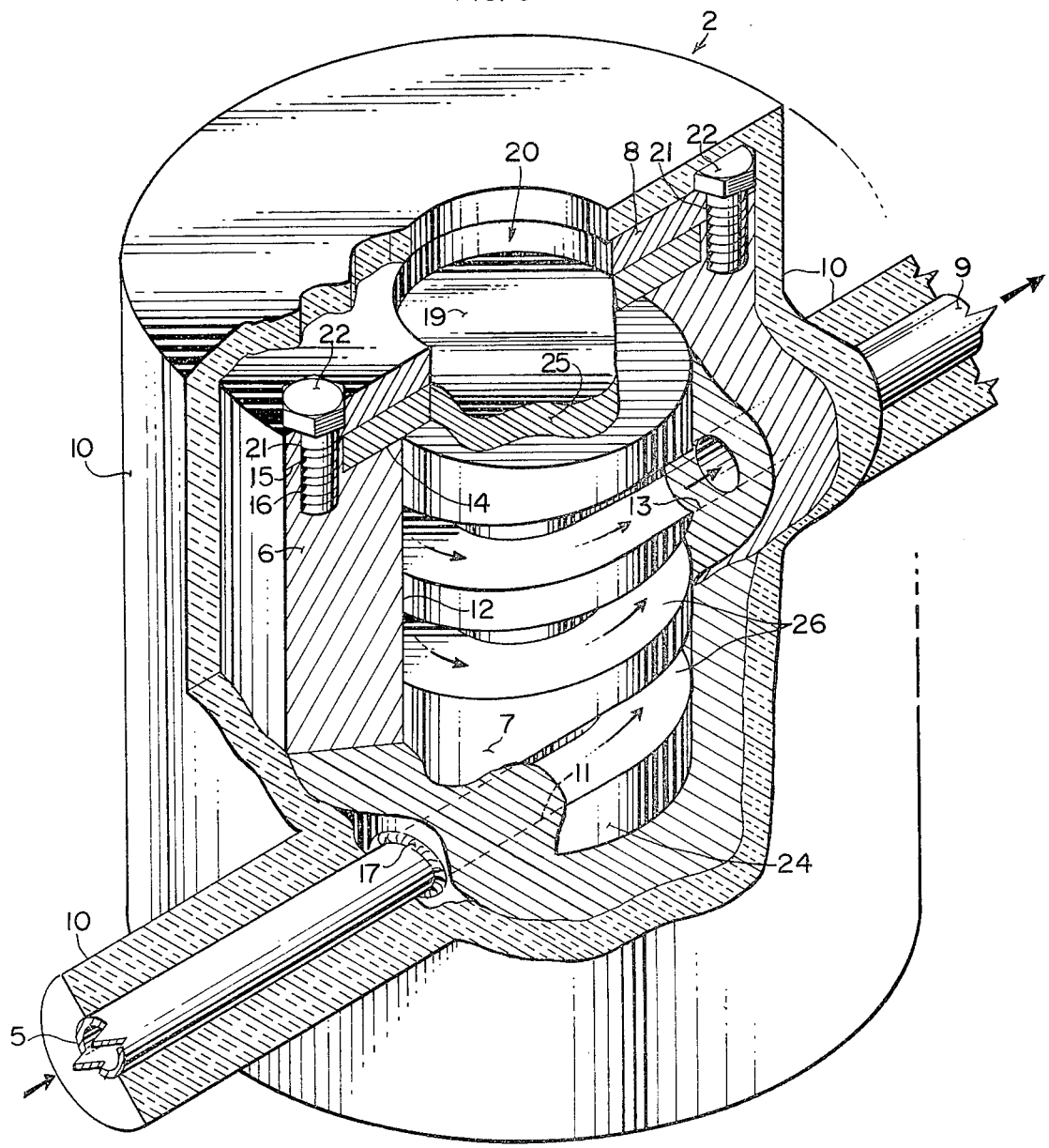
FIG. 7 is an enlarged perspective view of the heat conductor of the invention with portions of its outer surface removed to illustrate its inside.

FIG. 5 shows a number of solar heating apparatus 1 juxtaposed in a series of rows to form a modular panel 36. Apparatus 1 is connected to others by spot welding adjoining frames 3 together and by connecting the outlet conduit to the inlet conduit of the next apparatus. The inlet conduits of the first column of apparatus 1 are connected to an inlet manifold 37 and the outlet conduits of the last column of apparatus 1 are connected to an outlet manifold 38. Inlet manifold 37 and outlet manifold 38 are joined together by a connector 40. Connector 40 is secured to frame 3 by spot welds 39.

Each modular panel consist of twelve heat conductors 2 horizontally and twelve heat conductors 2 vertically giving a total of one hundred forty-four heat conductors 2 and Fresnel lens 4 positioned between inlet manifold 37 and outlet manifold 38. The heat produced by a single modular panel would determine the number of modular panels required to supply energy for a particular use, such as an electrical power station, industrial process heat, or space heating.

Figure 8:
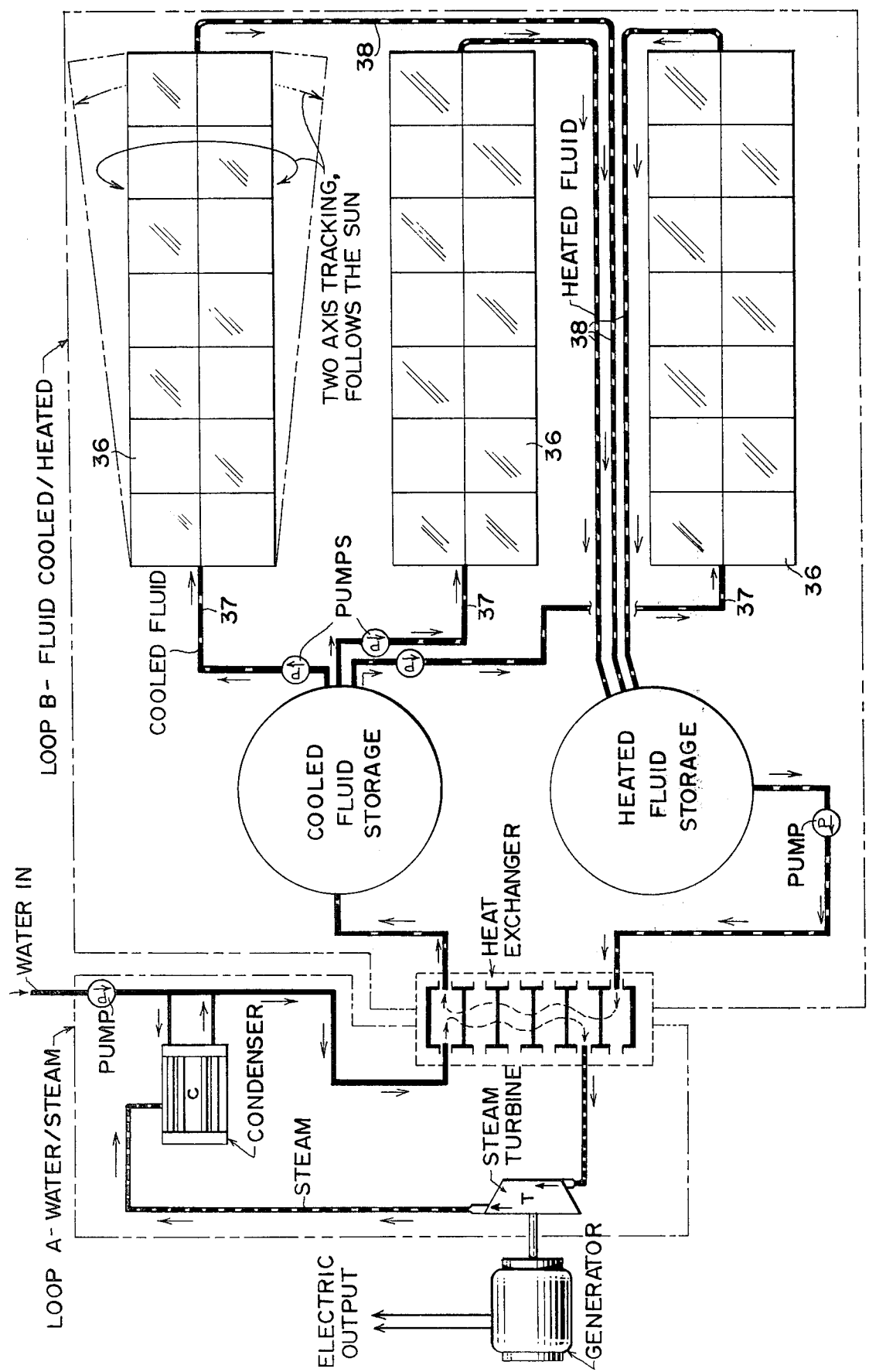
FIG. 8 is a schematic diagram of a heating system in which three modular panels of the invention are used.

FIG. 8 shows a system for generating electrical power. A heat transfer fluid, such as mineral oil, is stored in cooled insulated fluid storage tank. The fluid is pumped through inlet manifold 37 to the modular panels 36 where it is heated. The heated fluid traverses outlet manifold 38 to the insulated heated fluid storage tank. It is then pumped to the heat exchanger. The heat exchanger would be of the shell and tube type for steam generation. The heat exchanger generates steam that traverses to the impeller blades of the steam turbine. The heat transfer fluid traverses to the insulated cooled fluid storage for recycle. The steam turbine turns the generator for electrical power generation. Expended steam from steam turbine traverses through conduit to the condenser. Water from the condenser is added to water traversing through conduit for recycle. It will be understood that while the system shown is for generating electrical power, other uses of the heat produced by the solar heating apparatus modular panel are equally feasible.

Solar heating apparatus 1 has a length of twelve inches (30.48 cm), a width of twleve inches (30.48 cm), and a height of six inches (15.24 cm). Core 7 has a diameter of one inch (2.54 cm) and a height of one and a half inches (3.81 cm). Housing 6 has an outside diameter of two inches (5.08 cm) and a height of two inches (5.08 cm). Core 7 is of a slightly larger diameter than the inside diameter of housing 6 so that core 7 can be mechanically pressed into housing 6 to provide a seal between the spiral groove 26 and housing 6. Core 7 is pressed in place is such a manner that one end of spiral grooves 26 communicates with cylindrical opening 11 nd the other end communicates with cylindrical opening 13. The inside diameter of the inlet and outlet conduits 5 and 9 is one eighth inch (0.3175 cm). The inside diameter of the spiral grooves 26 is one fourth inch (0.635 cm). Fresnel lens 4 has a length of twelve inches (30.48 cm) and a width of twelve inches (30.48 cm).

My invention uses a Fresnel lens 4 to concentrate solar radiation onto top surface 19, which is positioned within the optimum focal point of the Fresnel lens 4. The temperature to which a heat transfer medium is heated is determined by the following factors: (1) Area of Fresnel lens, (2) size of inlet conduit, (3) rate of flow through a conductor, (4) number of conductors positioned between the inlet manifold and the outlet manifold, and (5) size of the outlet conduit.

A design using one square foot (929.03 cm$^2$) Fresnel lens, ⅛ in. ID inlet conduit, ¼ in. ID helical conduit, ⅛ in. (0.3175 cm) ID outlet conduit positioned in a row of twelve solar heating units would produce a temperature in excess of 1000° F. (537.78° C.).

A solar radiation concentration ratio of over 1000 to 1 is obtained by use of Fresnel lens. The concentration ratio is obtained by dividing the aperture area of the Fresnel lens by the area of the focal point of impinging solar radiation. Using a one square foot (929.03 cm$^2$) Fresnel lens which focus to a one eighth square inch area focal point of impinging solar radiation, a concentration ratio of 1152 is obtained (144÷0.125).

The helical conduit formed by spiral grooves 26 is intentionally made larger than the diameter of the inlet and outlet conduits to provide additional residence time for the heat transfer medium to absorb conducted radiation from the core. Using a ⅛ inch ID inlet conduit for heat transfer fluid inlet with a capacity of 10 ft./sec.

(304.8 cm/sec.) velocity would give a flow rate of 1.79 gal./min. (16.775 1/min.). Using a ¼ inch (0.635 cm) ID helical conduit and a ⅛ inch (0.3175 cm) ID outlet conduit would reduce flow rate due to larger diameter as fluid traverses to the outlet conduit thus offsetting the friction loss of sudden enlargement with sudden constriction loss. The diameter of the helical conduit should ideally be twice the diameter of the inlet and outlet conduits, but any ratio may be used so long as the diameter of the helical conduit is larger than the diameter of the inlet and outlet conduits.

The spiral grooves 26 which form the helical conduit provide maximum surface area for heat transfer of the impinging solar radiation onto the core to the heat transfer medium. Spiral grooves 26 revolve around the periphery of body 24 two and one half times in my invention. The amount of times spiral grooves 26 revolve around the periphery of body 24 is determined by the residence time desired for the heat transfer medium to absorb conductd radiation from the core. The residence time is determined by the size of the inlet conduit, helical conduit, and outlet conduit and by the length of the helical conduit as determined by the height of the body 24.

The length of a helical conduit formed by spiral grooves 26 which revolve around the periphery of body 24 two and one half times, with a one inch (2.54 cm) diameter body, is approximately seven inches. The seven inch (17.78 cm) length of the helical conduit provides a surface area of 5.25 square inches (33.873 cm$^2$) for heat transfer from the core to the heat transfer medium. When the solar heating apparatus 1 is mounted in a row of 12 units there will be a total length of fluid flow from the inlet manifold to the outlet manifold of nineteen feet (579.12 cm) with a total heated surface length of seven linear feet (213.36 cm) for the heat transfer of the traversing fluid. In addition, there will be an inside surface area of conduits from inlet manifold to outlet manifold of 121.82 square inches (785.983 cm$^2$) and a total inside surface area of helical conduit of 63 square inches (406.476 cm$^2$).

My invention can be used to generate steam by using water as the heat transfer medium or ideally using a thermal heat transfer medium such as Dowtherm, mineral oil, or molten inorganic salts. In using a thermal heat transfer medium such as Dowtherm, mineral oil, Therminol, or molten salts in conjunction with a heat pipe system, the heat can be transported and transferred up to 500 times as much thermal energy per unit weight as a thermal conductor with the same cross section. By appropriate selection of working fluids, heat pipes have been designed and operated at temperatures ranging from cryogenic temperatures up to 2250° F. (1232.22° C.).

Solar heating apparatus 1 juxtaposed with others to form modular panel 36. Modular panel 36 includes twelve solar heating apparatus 1 juxtaposed horizontally and twelve solar heating apparatus 1 juxtaposed vertically, a total of 144 solar heating apparatus 1, positioned between the inlet manifold and the outlet manifold.

Modular panel 36 is mounted on a two axis tracking structure (not shown) so that top surface 19 is maintained at the optimum angle for the impinging solar radiation to be focussed by the Fresnel lens 4 onto it. The tracking device operates by photo-electric cells placed at each corner of the tracking structure and connected to suitable electric motors that drive the two axis tracking device.

The solar radiation normal to a trackig surface is constant to within 10% for some six to ten hours per day. The utilization of a tracking device with modular panel 36 provides approximately 90% of the incident energy. Comparable systems such as a compound Parabolic Collector— Flat-Plate Collector is able to provide roughly 64% of the incident energy. The cost of manufacturing my invention is approximately 25% to 35% less than the Power Tower, Helio Stat Concept, or the Compound Parabolic Collector Concept. The Fresnel lens is manufactured by the injection molding process using a clear Polycarbonate Resin. The housing and the core are manufactured on a turret lathe. The frame is made from a metal stamping die and simply spot welded into place. Using these processes one could manufacture the total solar collection system for approximately $7.50 per square foot.

One of the most critical problems with solar energy collector design concepts is the overall efficiency of the collector as well as the heat transfer properties and the economics of manufacturing. My invention has an efficiency of 80% of the total insolation, e.g., 10% loss of incident energy, 3% radiation loss, 5% convection loss, and 2% insulation loss. Heat loss is minimized by the use of solid insulation to insulated the heat conductor except for the center opening, which allows impinging focused solar radiation onto the top surface.

FIG. 8 shows the top modular panel 36 rotating in two directions by a two axis tracking device which tracks the movement of the sun and moves the Fresnel lenses so that they are properly oriented with respect to the sun to reflect solar energy onto the heat conductors.

Each modular panel of my invention would be mounted upon a two axis tracking device to use approximately 90% of the incident energy. The heat produced by a modular panel would determine the number of panels required to supply energy for a particular use, such as an electrical power station, industrial process heat, or space heating.

Although but a single embodiment of the invention has been disclosed and described herein, it is obvious that many changes may be made in the size, shape, arrangements, color and detail of the various elements of the invention without departing from the scope of the novel concepts of the present invention.

I claim as my invention:

1. A solar heating apparatus comprising a heat conductor, a frame, and a Fresnel lens; the heat conductor is secured to the bottom portion of the frame and the Fresnel lens is secured to the top portion of the frame; the heat conductor is positioned substantially within the focal point of the Fresnel lens when the heat conductor is secured to the frame; the heat conductor includes an inlet conduit, a housing, a core, a pressure plate, and an outlet conduit; the housing includes an inlet opening, a central opening, an outlet opening, an inner flange, an outer flange, and two connector openings; the inlet conduit is in communication with the inlet opening and the outlet conduit is in communication with the outlet opening; the core includes a cylindrical body with a helical conduit revolving around its periphery and a head; the cylindrical body of the core fits within the central opening of the housing so that one end of the helical conduit communicates with the inlet opening and the other end of the helical conduit communicates with the outlet opening; the pressure plate includes a center opening and two connector openings; the pressure plate is secured to the outer flange by two bolts which pass through the connector openings of the pressure plate and the housing in order to secure the core within the housing; the center opening of the pressure plate allows impinging focused solar radiation onto the top of the core; insulation coats the heat conductor except for the center opening of the pressure plate; the frame includes a bottom portion, a side portion, a top portion, and a connector portion; the bottom portion includes four angles which are connected at their ends to form a rectangular structure; the side portion includes four angles which are placed and secured upright to the corners of the bottom portion; the top portion includes four angles which are connected at their ends to form a rectangular structure and are secured to the side portion; the connector portion includes two spaced angles which are secured at their ends to the bottom portion; the angles of the connector portion are spaced so that the heat conductor fit within the legs of the angles and is secured thereto; Fresnel lens is secured to the top portion of the frame by means of fasteners which are punched out of the top portion.

2. The solar heating apparatus of claim 1, wherein the inside diameter of the helical conduit is larger than the inside diameter of the inlet and outlet conduits.

3. The solar heating apparatus of claim 1, wherein a number of solar heating apparatus are juxtaposed in a row and are joined together so that a fluid or gas may pass through them from an inlet and leave them through an outlet.

4. The solar heating apparatus of claim 3, wherein a predetermined number of solar heating apparatus are juxtaposed in a series of rows to form a modular panel; the inlet conduits of the first column of solar heating apparatus are connected to an inlet manifold and the outlet conduits of the last column of solar heating apparatus are connected to an outlet manifold.

5. The solar heating apparatus of claim 4, wherein the inlet manifold and the outlet manifold are joined together by a connector which is secured to the frames of the solar heating apparatus and the modular panel is adapted to be mounted on a two axis tracking device.

6. The solar heating apparatus of claim 2, wherein the inside diameter of the helical conduit is twice the diameter of the inlet and outlet conduits and the diameter of the cylindrical body of the core is slightly larger than the diameter of the central opening of the housing.

* * * * *